(12) United States Patent
Chung et al.

(10) Patent No.: US 6,984,496 B2
(45) Date of Patent: Jan. 10, 2006

(54) VITRO ASSAY FOR TESTING GABAPENTINOID ACTIVITY

(75) Inventors: Fu-Zon Chung, Ann Arbor, MI (US); Yulong Hong, Painted Post, NY (US)

(73) Assignee: Warner-Lambert Company, Morris Plains, NJ (US)

( * ) Notice: Subject to any disclaimer, the term of this patent is extended or adjusted under 35 U.S.C. 154(b) by 7 days.

(21) Appl. No.: 10/057,099

(22) Filed: Jan. 24, 2002

(65) Prior Publication Data

US 2002/0106633 A1 Aug. 8, 2002

Related U.S. Application Data

(60) Provisional application No. 60/266,358, filed on Feb. 2, 2001.

(51) Int. Cl.
*G01N 33/53* (2006.01)
*G01N 33/567* (2006.01)
*C07C 229/00* (2006.01)
*C07C 315/00* (2006.01)

(52) U.S. Cl. .......................... 435/7.2; 435/7.1; 562/507
(58) Field of Classification Search ................ 562/507; 435/7.1, 7.2, 69.1, 252.3, 471
See application file for complete search history.

(56) References Cited

U.S. PATENT DOCUMENTS 6,001,581 A 12/1999 Johnson et al. ............ 435/7.21

FOREIGN PATENT DOCUMENTS

WO 9216547 1/1992

OTHER PUBLICATIONS

Sharif and Sharif, "A high throughput system for the evaluation of protein kinase C inhibitors based on Elk 1 transcriptional activation in human astrocytoma cells", *International Journal of Oncology*, vol. 14, 1999, pp. 327–335.

Fiore et al., "Activation of p42 Mitogen–Activated Protein Kinase by Glutamate Receptor Stimulation in Rat Primary Cortical Cultures", *Journal of Neurochemistry*, vol. 61, No. 5, 1993, pp. 1626–1633.

Sharif, "Mitogenic signaling by substance P and bombesin–like neuropeptide receptors in astrocytic/glial brain tumor–derived cell lines (Review)", *International Journal of Oncology*, vol. 12, 1998, pp. 273–286.

Lewis, et al., "Signal Transduction Through Map Kinase Cascades", *Advances In Cancer Research*, vol. 74, 1998. pp 49–139.

Pin and Duvoisin, "Review†: Neurotransmitter receptors I The Metabotropic Glutamate Receptors: Structure and Functions", *Neuropharmacology*, vol. 34, No. 1, 1995, pp. 1–26.

Morris, "Gabapentin", *Epilepsia*, vol. 40 (Suppl 5), 1999, pp S63–S70.

Ferrier, "Lamotrigine and Gabapentin: Alternatives in the Treatment of Bipolar Disorder", *Neuropsychobiology* vol. 38, 1998, pp. 192–197.

Bryans, et al., "Identification of Novel Ligands for the Gabapentin Binding Site on the $\alpha_2\delta$ Subunit of a Calcium Channel and Their Evaluation as Anticonvulsant Agents", *Journal of Medicinal Chemistry*, vol. 41, No. 11. 1998, pp. 1838–1845.

Purpura, et al., "Structure–Activity Determinants of Pharmcological Effects of Amino Acids and Related Compounds on Central Synapses", *Neurochemistry*, vol. 3, 1959, pp 238–268.

Spokes, "Gaba in Huntington's Chorea, Parkinsonism and Schizophrenia", *Adv Exp Med Biol*, vol. 123, 1978. pp. 461–473.

Wu, et al., "Abnormalities of Neurotransmitter Enzymes in Huntington's Chorea", *Neurochemical Research*, vol. 4, No. 5, 1979, pp. 575–586.

Tian, et al., "Structural Motifs Encoded by Individual Exons of the Human Neurokinin–1 Receptor Gene Interact Differentially with Selective Agonists and Antagonists", vol. 67, 1996, pp 1191–1199.

Bryans, et al., "3–Substituted GABA Analogs with Central Nervous System Activity: A Review", *Medical Research Review*, vol. 19, 1999, pp 149–177.

Hoekstra, et al., "Chemical Development of CI–1008, an Enantiomerically Pure Anticonvulsant", *Organic Process Research & Development*, vol. 1,1997, pp 26–38.

*Primary Examiner*—Robert Landsman
(74) *Attorney, Agent, or Firm*—Charles W. Ashbrook; Mehdi Ganjeizadeh

(57) ABSTRACT

An assay and method for selecting analogs and derivatives of gabapentin based on the compounds inhibitory activity toward MAP kinase and MAP kinase mediated reporter gene expression. The method includes the steps of activating the MAP kinase signaling pathway, detecting the MAP kinase signal, and screening the gabapentin analogs and derivatives for inhibitory activity against the MAP kinase signal.

11 Claims, 8 Drawing Sheets

Inhibitory effect of gabapentin on ERK-2 phosphorylation in CHO cells transfected with mGluR5

Effect of Gabapentin and Pregabalin on NK1 Mediated
ELK1 Activation in NK1 / CHO Cells: dose response Effect of Gabapentin and Pregabalin on NK1 Mediated ELK1 Activation in NK1/CHO Cells: dose response Concentration of Gabapentin (microMolar)

Effect of Gabapentin and Pregabalin on NK1 Mediated ELK1 Activation in NK1/CHO Cells: dose response Concentration of Pregabalin (microMolar)

FIG. 4A

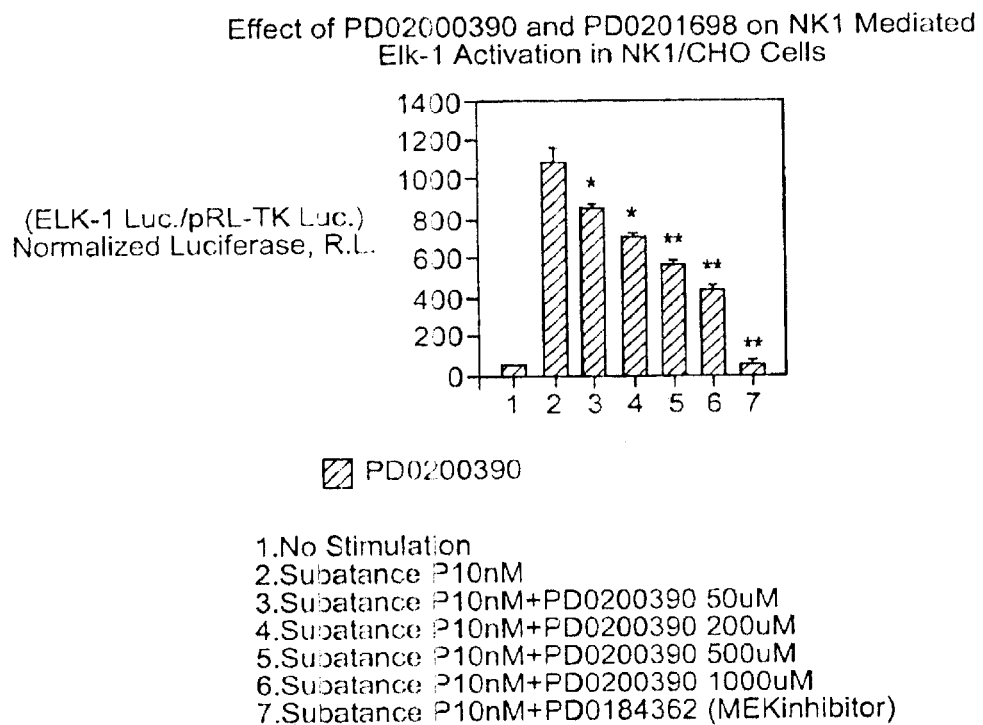

Effect of PD02000390 and PD0201698 on NK1 Mediated Elk-1 Activation in NK1/CHO Cells 1. No Stimulation
2. Subatance P 10nM
3. Subatance P 10nM+PD0200390 50uM
4. Subatance P 10nM+PD0200390 200uM
5. Subatance P 10nM+PD0200390 500uM
6. Subatance P 10nM+PD0200390 1000uM
7. Subatance P 10nM+PD0184362 (MEKinhibitor)

FIG. 4B

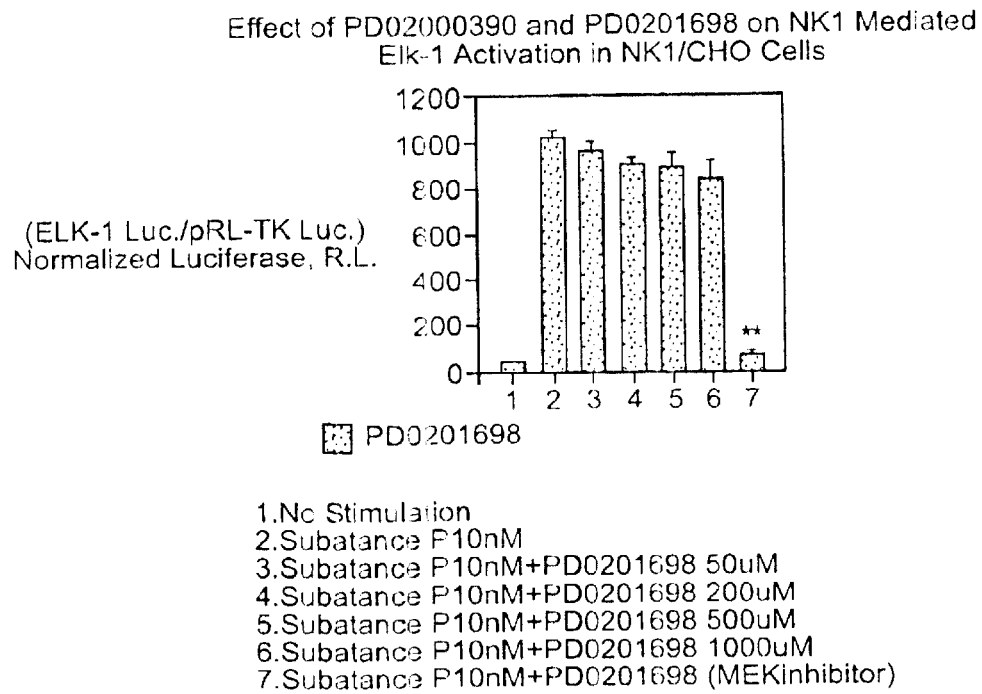

Effect of PD02000390 and PD0201698 on NK1 Mediated Elk-1 Activation in NK1/CHO Cells 1. No Stimulation
2. Subatance P 10nM
3. Subatance P 10nM+PD0201698 50uM
4. Subatance P 10nM+PD0201698 200uM
5. Subatance P 10nM+PD0201698 500uM
6. Subatance P 10nM+PD0201698 1000uM
7. Subatance P 10nM+PD0201698 (MEKinhibitor)

Inhibition of Gabapentin on PMA Stimulated Elk-1 activation in IMR 32 Cells

1. No Stimulation
2. PMA 50nM
3. PMA 50nM+Gabapenin 50uM
4. PMA 50nM+Gabapenin 100uM
5. PMA 50nM+Gabapenin 200uM
6. PMA 50nM+Gabapenin 600uM Inhibitory Effect of Gabapentin on NK1 Mediated SRE Activation in CHO/NK1 cells 1. No Stimulation
2. Subatance P 10nM
3. Subatance P 10nM+Gabapentin 50uM
4. Subatance P 10nM+Gabapentin 250uM
5. Subatance P 10nM+Gabapentin 500uM
6. Subatance P 10nM+Gabapentin 1000uM

VITRO ASSAY FOR TESTING GABAPENTINOID ACTIVITY

This application is a utility application which claims benefit of U.S. Provisional Application 60/266,358 filed Feb. 2, 2001; the entire contents of which is hereby incorporated herein by reference.

FIELD OF THE INVENTION

The present invention relates generally to assays that test analogs and derivatives of γ-aminobutyric acid (GABA) for their ability to modulate mitogen-activated protein kinase (MAP Kinase) activity, and more particularly, but not by way of limitation, to an in vitro screening assay for selecting analogs and derivatives of 1-(aminomethyl) cyclohexaneacetic acid (gabapentin) based on the analogs' inhibitory activity toward Elk-1.

BACKGROUND OF THE INVENTION

GABA is a neurotransmitter involved in normal regulation of the mammalian central nervous system. An imbalance in GABA concentrations in the central nervous system has been implicated in several disease states, including; seizures, Huntington's chorea, Parkinson's disease, spasticity, and neuropathic pain. Treatment of these disease states has generally centered on increasing GABA concentrations in the afflicted patient's central nervous system. Purpura et al., Neurochem, 1959;3:238–268; Spokes., *Adv. Exp. Med. Biol.*, 1978:123:461–473; Wu et al., *Neurochem. Res.*, 1979;14:575–586. Unfortunately, direct treatment of afflicted patients with GABA has proven ineffective as GABA has physiochemical properties that prohibit it from crossing the blood-brain barrier.

Structurally related compounds to GABA are being pursued as possible treatments for GABA mediated disorders. Gabapentin (1-(aminomethyl) cyclohexaneacetic acid) is one such structurally related compound which is known to readily cross the blood-brain barrier and bind throughout the central nervous system. Gabapentin is currently used in the treatment of seizures and epilepsy and has been implicated as a possible treatment in other GABA mediated central nervous system disorders.

There is a need in the relevant art to have additional compounds that have gabapentin like activity. Other gabapentin related drugs may be more effective than gabapentin in treating seizures and other central nervous system disorders, or may be used in patients that have become refractory to gabapentin over time or have unwanted side effects. Against this backdrop the present invention has been developed.

SUMMARY OF THE INVENTION

The present invention provides an in vitro assay for screening compounds that are structurally related to gabapentin for MAP kinase inhibitory activity. It is envisioned that the present invention could be used as a general screening procedure in obtaining novel gabapentinoids for use in treatment of disorders of the central nervous system and neuropathic pain.

In one aspect, the present invention is a method for detecting MAP kinase inhibitory activity by compounds that are structurally related to gabapentin. In one preferred embodiment, NK expressing cells are stimulated with substance P which results in the phosphorylation of the MAP kinase member, Erk-2. In another preferred embodiment, mGluR expressing cells are stimulated with quisquolate which results in the phosphorylation of Erk-2. To screen for gabapentinoid activity, test substances are individually incubated with the activated cells and Erk-2 phosphorylation determined. In preferred embodiments, Erk-2 phosphorylation after treatment with a test compound is compared to activated cells treated with a similar concentration of gabapentin.

In another aspect, the present invention is a method for testing a compound for gabapentinoid activity by determining its effects on a MAP kinase inducible reporter gene. In one preferred embodiment, cells are engineered to incorporate reporter constructs under the control of a MAP kinase inducible transcription factor. In one preferred embodiment, NK expressing cells are engineered to incorporate a reporter gene under the transcriptional control of an Ets family member, for example Elk-1, where the Ets family member is activated by activated Erk-2. In another embodiment of the present invention, mGluR expressing cells are engineered to incorporate reporter construct under the transcriptional control of an Ets family member, for example Elk-1.

In another aspect, the present invention is a treatment for neuropathic pain where compounds structurally related to gabapentin are screened for Elk-1 inhibitory activity in the assays discussed above, and compounds having inhibitory activity administered to a subject.

Finally, in another aspect, the present invention is a treatment for central nervous system disorders compounds structurally related to gabapentin are screened for Elk-1 inhibitory activity in the assays discussed above, and compounds having inhibitory activity administered to a subject.

BRIEF DESCRIPTION OF THE DRAWINGS

FIG. 4 are graphs showing the dose-dependent effects of PD 200390 and PD 201698 on NK1 mediated Elk-1 transcription. Relative light units (Y axis) indicate luciferase activity in the presence of increasing concentrations of PD 200390 or PD 201698 (Y axis). PD 184352, a potent MEK inhibitor, was also included in the assay as a positive control.

DETAILED DESCRIPTION OF THE INVENTION

Definitions

Figure 1:
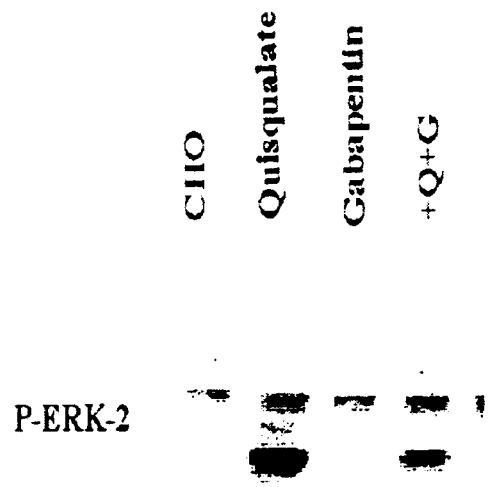
FIG. 1 shows the inhibitory effects of gabapentin on NK1 mediated Erk-2 phosphorylation. Chinese Hamster Ovary (CHO) cells expressing rat mGluR5 receptors were pretreated with gabapentin (100 μM) for 30 minutes and than stimulated with quisquolate (100 μM) for 10 minutes. Products from treated cells were analyzed by Western blotting with anti-pErk antibody.

The following definitions are provided to facilitate understanding of certain terms used frequently herein and are not meant to limit the scope of the present disclosure.

As used herein "amino acids" mean any of the 20 gene encoded amino acids as well as any modified amino acid sequences. Modifications may include natural processes such as posttranslational processing, or may include chemical modifications which are known in the art. Modifications include but are not limited to: ubiquitination, acetylation, amidation, covalent attachment of flavin, ADP-ribosylation, cross linking, iodination, methylation, etc.

As used herein, "control cell" refers to a cell that has been cultured in parallel with a cell treated under the specified experimental condition; but unlike the treated cell, the control cell has not undergone the specified experimental condition. Control cells represent a baseline from which comparisons are made.

The term "Elk-1" as used herein is meant to refer to the $p62^{TCF}$ transcription factor shown to be activated by Erk, JNK/SAPK, or p38 MAPK. Elk-1, among other things, regulates serum response element transcription through an interaction with serum response factor. For purposes of this disclosure, the term Elk-1 also includes transcription factors that are substantially the same as Elk-1 but that have minor substitutions, deletions, or additions to the Elk-1 polypeptide sequence.

The term eukaryotic cell line is used to refer to cells established in ex vivo culture. It is a characteristic of the eukaryotic cell line of the present invention that it be capable of supporting MAP kinase signaling. Examples of suitable eukaryotic cells within the context of the present invention include SF9 insect cells (Summers and Smith., Texas Agricultural Experiment Station Bulletin, 1987;1555), CHO cells (Puck et al., J. Exp. Med., 1958;108:945–955) including CHO K1, human cervical carcinoma (Hela) cells (ATCC CCL 2), monkey kidney CV1 line transformed by SV40 (COS-7) cells (ATCC CRL 1651), human embryonic kidney (HEK293) cells (Graham et al., J. Gen. Virol., 1977;36:59), human neuroblstoma (IMR-32) cells (ATCC CCL-127), etc.

The term "expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., Molecular cloning: A laboratory manual, 1989;18.1–18.88).

The term "gabapentin" refers to 1-(aminomethyl) cyclohexaneacetic acid as described in U.S. Pat. No. 4,024,175.

The term "gabapentinoid" or "gabapentinoids" refers to analogs and derivatives of gabapentin as well as to compounds that show gabapentin-like inhibitory activity within the context of embodiments of the present invention.

The term "mGluR" as used herein is meant to refer to the family of G-protein-coupled receptors known as the metabotropic glutamate receptors. This family includes Group I mGluRs, mGluR1 and mGluR5, Group II mGluRs, mGluR2 and mGluR3, and Group III mGluRs, all others. (Pin et al., Neuropharmacology, 1995;34:1–26.)

The term "modulation" as used herein is meant to refer to either upregulating or downregulating the activity of a protein.

The term "nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

The term "polynucleotide" refers to a linear sequence of nucleotides. The nucleotides are either a linear sequence of polyribonucleotides or polydeoxyribonucleotides, or a mixture of both. Examples of polynucleotides in the context of the present invention include: single- and double-stranded DNA, single- and double-stranded RNA, and hybrid molecules that have both mixtures of single- and double-stranded DNA and RNA. Further, the polynucleotides of the present invention may have one or more modified nucleotides.

As used herein, "protein," "peptide," and "polypeptide" are used interchangeably to denote an amino acid polymer or a set of two or more interacting or bound amino acid polymers.

The term "substance P" refers to a tackykinin neuropeptide that acts through the $NK_1$, $NK_2$, and $NK_3$ receptors.

The term "vector," "extra-chromosomal vector," or "expression vector" refers to a first piece of DNA, usually double-stranded, which may have inserted into it a second piece of DNA. Foreign DNA is defined as heterologous DNA, which is DNA that may or may not be naturally found in the host cell and includes additional copies of nucleic acid sequences naturally present in the host genome. The vector transports the foreign DNA into a suitable host cell. Once in the host cell, the vector may be capable of integrating into the host cell chromosomes. The vector may also contain the necessary elements to select cells containing the integrated DNA as well as elements to promote transcription of mRNA from the transfected DNA. Examples of vectors within the scope of the present invention include, but are not limited to, plasmids, bacteriophages, cosmids, retroviruses, and artificial chromosomes.

Modes for Carrying out the Invention

The present invention is based upon, among other things, the discovery of a novel in vitro assay for testing compounds for gabapentinoid activity. In particular, the invention relates to the discovery that under certain conditions cells respond to gabapentin, and compounds having gabapentin like activity, through the inhibition of the MAPK signaling pathway. In preferred embodiments, cells are engineered to express components of the MAPK signaling pathway, for example neurotransmitters and G-protein coupled receptors, so that stimulation of the component leads to activation of target MAK kinases, for example activation of Erk-2. In preferred embodiments, cells used in the in vitro assay are engineered to express both components of the MAPK signaling pathway as well as reporter constructs under the inducible control of activated Erk-2, for example, a luciferase construct under the control of the Elk-1 transcription factor. The engineered cells are used in testing compounds for gabapentinoid activity by detecting the compound's inhibitory effects on the activated MAPK signaling pathway.

The in vitro analysis of gabapentinoid activity is of importance in detecting novel gabapentinoids in an inexpensive in vitro assay. Compounds that have gabapentinoid activity in the present invention may then be further tested for activity in in vivo studies and eventually patient studies.

Analysis of gabapentinoid activity is not limited to gabapentinoid activity on Erk-2 phosphorylation or Elk-1 mediated reporter gene expression, it may also be determined using other direct and indirect analysis of Elk-1, as well as through direct or indirect analysis of the MAPK signaling pathway.

Note that within this application, unless otherwise stated, the techniques utilized may be found in any of several well-known references such as: Sambrook et al., Molecular cloning: A Laboratory Manual, 1989; Goeddel D, eds., Gene Expression Technology, Methods in Enzymology Academic Press: San Diego, Calif., 1991;185; Deutshcer M. P., Guide to Protein Purification. In: Methods in Enzymology. $3^{rd}$ ed. Academic Press, Inc., 1990; Innis et al., PCR protocols: A guide to methods and applications Academic Press: San Diego, Calif., 1990; Freshney R. I., Culture of animal cells: A manual of basic technique. $2^{nd}$ ed., New York: Liss, Inc., 1987; and Murray E. J., ed., Gene Transfer and Expression Protocols. Clifton, N.J.: The Humana Press Inc., 109–128.

Vectors and Host Cells

In general, embodiments of the present invention may be implemented through the transient expression of the foreign DNA or through the stable integration of the foreign DNA into target cells. Techniques required for this aspect of the invention are well-known in the art (Sambrook et al. Molecular cloning: A laboratory manual. $2^{nd}$ ed., Cold Spring Harbor Press, 1989) and can include calcium phosphate transfection, dextran sulfate transfection, electroporation, lipofection, and viral infection (Graham and van der Eb. Virology, 1978;52;456–457; Chisholm et al., DNA cloning IV: A practical approach, mammalian systems, Glover and Hanes, eds., 1995;141; Andreason., *J. Tisss. Cult. Meth.*, 1993;15:56–62).

In an aspect of the present invention, novel polynucleotides substantially similar to the Group I mGluRs are subcloned into an extra-chromosomal vector. The subcloned polynucleotide(s) may be joined to a vector having a cis-acting or regulatory element for increased propagation in a host cell (note that the transacting factors involved are supplied to the host, supplied by a second vector or supplied by the vector itself upon introduction into the host). This aspect of the invention allows for the in vivo and in vitro expression of either mGluR1 or mGluR5.

It is further envisioned that novel polynucleotides substantially similar to the NK1, NK2, or NK3 receptor are subcloned into an extra-chromosomal vector. The subcloned polynucleotides may be joined to a vector having a cis-acting or regulatory element for increased propagation in a host cell (note that the transacting factors involved are supplied to the host, supplied by a second vector or supplied by the vector itself upon introduction into the host). This aspect of the invention allows for the in vivo and in vitro expression of either NK1, NK2, or NK3.

It is further envisioned that novel polypeptides substantially similar to Elk-1 or GAL4-Elk-1 are subcloned into an extra-chromosomal vector. The subcloned polynucleotides may be joined to a vector having a cis-acting or regulatory element for increased propagation in a host cell (note that the transacting factors involved are supplied to the host, supplied by a second vector or supplied by the vector itself upon introduction into the host). This aspect of the invention allows for the in vivo and in vitro expression of either Elk-1 or the fusion protein GAL4-Elk-1.

Several vectors can be used in the context of this invention, including: PcDNA3 vector (Invitrogen), vectors having the T3 and T7 polymerase promoters, vectors having the SV40 promoter, or the CMV promoter, pTRE2 vector used in the Tet-on™ inducible expression system (Clontech labs), the pFA2-Elk-1 plasmid (Stratagene), pFR-Luc plasmid (stratagene), pCDNA3.1/Hygro (Invitrogen), or any other promoter that either can direct expression of a polypeptide off a polynucleotide, or that one wishes to test for the ability to direct expression of a polypeptide off a polynucleotide.

The host cells of the present invention may be of any type, including, but not limited to, noneukaryotic and eukaryotic cells. Host cells are cultured using standard tissue culture techniques in conventional media as is well-known in the art. The level of expression of the DNA introduced into a host cell of the invention depends on multiple factors, including gene copy number, efficiency of transcription, messenger RNA a desired polypeptide according to the present invention will typically involve optimizing one or more of those factors.

In Vitro Gabapentinoid Activity Assay and Method

In one aspect, the present invention provides an in vitro assay by which target compounds are tested or screened for gabapentinoid activity by determining the compounds inhibitory effects on Elk-1 mediated reporter gene expression.

NK Receptor

The in vitro assay is based on the principle that activated NK-1, NK-2, or NK-3 (or any combination of the three receptors) stimulate Erk-2 activity. Activated Erk-2, among other things, activates any number of proteins belonging to the Ets family of helix-turn-helix transcription factors, for example Elk-1. In the present invention, NK expressing cells are engineered to incorporate reporter constructs, for example vectors having the luciferase gene, under the transcriptional control of an Ets family member, preferably Elk-1. Compounds having gabapentinoid activity are ultimately detected and quantitated through inhibition of Elk-1 mediated reporter gene expression.

In a preferred embodiment of the present invention, the NK receptor is the NK-1 receptor, and the reporter construct has one or more serum response elements or CREB (cAMP response element binding protein) elements that are recognized by Elk-1. Stimulation of the NK-1 receptor with agonist, for example substance P, results in the activation of Erk-2, and hence the activation of Elk-1. Activated Elk-1 binds to the response elements and induces reporter gene expression. Typical agonist concentrations are from 0.1 to 100 nM, and preferably from 1 to 10 nM. Suitable reporter genes for use with the present invention include, but are not limited to, the luciferase gene, chloramphenicol acetyltransrerase gene, β-galactosidase gene, and β-lactamase gene.

A preferred NK1 expressing cell line for use in the present invention is one that is stably transfected with recombinant DNA comprising the NK1 receptor (or the NK2 or NK3 receptors or multiples of NK1, NK2, or NK3 receptors) (see Tian Y. et al., *J. Neurochem.*, 1996;67:1191–1199). Recombinant cell lines are quantitated for NK1 receptor expression by employing assays for NK1 biological activity or by employing assays that are independent of such activity, such as Western blotting or immunoassay using antibodies that are capable of reacting with NK1. (Sambrook et al., Molecular Cloning: A Laboratory Manual, 1989;18.1–18.88)

Another preferred cell line for use with the present invention is a NK expressing cell line stably transfected with recombinant DNA substantially comprising the Gal4/Elk-1 fusion transcription factor, and that further has copies of a Gal4-controlled reporter construct. In these cases, activation of the Elk-1 portion of the fusion protein through the MAP kinase signaling pathway leads to Gal4 controlled expression of the reporter gene. MAP kinase activation of the Elk-1 fusion protein causes the protein to bind to the Gal-4 binding sites on the reporter gene and induce reporter construct expression. Note that other Elk-1 fusion protein/reporter gene construct pairs may be used in the context of the present invention as long as NK mediated activation of the MAP kinase pathway induces the Elk-1 fusion protein to express the reporter construct.

Target compounds to be screened in the above described in vitro assay are synthesized as described in international patent application WO 9921824, which is herein incorporated by reference. Compounds may be incubated with cells prior to, at the same time, or after stimulation of the NK receptor with a NK receptor agonist. In a preferred embodiment, incubation of the compound(s) with the above described cells occurs prior to NK receptor activation, suitable compound incubation times prior to NK activation are variable, but 30 to 45 minutes is typical. Total incubation times of target compounds on the host cells is variable and set for the user's convenience as well as for the level of reporter construct expression needed for detection in the users laboratory; however, suitable times are typically about 3 to 6 hours, and more preferably about 3.5 to 5 hours.

WO 9921824, is now issued as U.S. Pat. No. 6,635,673. Both WO 9921824, and U.S. Pat. No. 6,635,673 disclose, in the first paragraph under DETAILED DESCRIPTION OF THE INVENTION, that "[t]he compounds of the instant invention and their pharmaceutically acceptable salts are as defined by formulas 1 and 1A

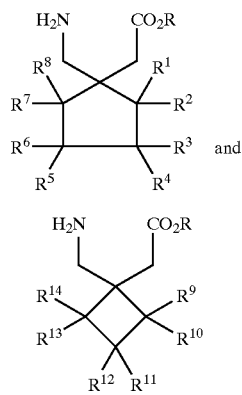

or a pharmaceutically acceptable salt thereof wherein:
R is hydrogen or a lower alkyl; $R^1$ to $R^{14}$ are each independently selected from hydrogen, straight or branched alkyl of from
1 to 6 carbons, phenyl, benzyl, fluorine, chlorine, bromine, hydroxy, hydroxymethyl, amino, aminomethyl, trifluoromethyl, $-CO_2H$, $-CO_2R^{15}$, $-CH_2CO_2H$, $-CH_2CO_2R^{15}$, $-OR^{15}$ wherein
$R^{15}$ is a straight or branched alkyl of from 1 to 6 carbons, phenyl, or benzyl, and $R^1$ to $R^8$ are not simultaneously hydrogen". Both WO 9921824, and U.S. Pat. No. 6,635,673 disclose that "[t]he compounds of the invention show good binding affinity to the $\alpha_2\delta$ subunit. Gabapentin (Neurontin®) is about 0.10 to 0.12 μM in this assay. Since the compounds of the instant invention also bind to the subunit, they are expected to exhibit pharmacological properties comparable to gabapentin." See WO 9921824, lines 5 to 9, page 18; and U.S. Pat. No. 6,635,673, column 13, paragraph 2.

In general, each compound is tested for inhibitory activity through a range of concentrations, for example, a compound may be incubated on a series of independent groups of cells, where each group of cells receives a varying concentration of compound, from 25 to 1500 μM, and preferably from 50 to 1000 μM. In some embodiments of the present invention, the host cells are incubated with a single dose of target compound, for example, a single dose between 25 and 1500 μM, and preferably a single dose of about 450 to 550 μM.

With respect to the detection of reporter expression in the presence and absence of the tested compound, cells are harvested and reporter gene expression determined. Luciferase assays are performed according to the procedures suggested by the manufacture (Promega, Wis.), and procedures for other common reporter gene assays are well-known in the art. Percent reporter gene inhibition is correlated with gabapentinoid activity, where the stronger the gabapentinoid activity the greater the percent reporter inhibition. Although compounds showing any level of inhibition, above a known negative control, are considered positive for gabapentinoid activity, compounds that show at least 20%, preferably 25%, and most preferably 30% inhibition at 500 μM are considered hits and will be identified as having gabapentinoid activity. Note also that comparisons may be made between the target compound and similarly treated gabapentin, where a hit is a compound having an inhibitory activity similar to or greater than gabapentin activity in the assay. Note also, where a compound is tested over a concentration range, a preferable response is one that is dose responsive.

mGluR

In another aspect, the in vitro assay is based on the principle that activated Group I mGluR receptors stimulate Erk-2 activity. Activated Erk-2, among other things, phosphorylates and activates any number of proteins belonging to the Ets family of helix-turn-helix transcription factors, for example Elk-1. Activated Elk-1 induces reporter gene expression which can be followed in the presence and absence of compounds, where compounds having gabapentinoid activity inhibit Elk-1 inducible reporter expression.

In a preferred embodiment of the present invention, the reporter construct has one or more serum response elements or CREB (cAMP response element binding protein) binding sites. Stimulation of mGluR1 or mGluR5 (or a combination of the two) with agonist, for example quisqualic acid, results in activation of Erk-2, and hence activation of Elk-1. Suitable quisqualic acid concentrations for use with the present invention are from 10 to 500 μM, and are preferably from 50 to 200 μM. Activated Elk-1 binds to the serum response elements or CREB elements on the reporter construct and induces reporter gene expression. Suitable reporter genes for use with the present invention include, but are not limited to, the luciferase gene, chloramphenicol acetyltransrerase gene, β-galactosidase gene, and β-lactamase gene.

In another preferred embodiment of the present invention, host cells are constructed to stably express a Gal4-Elk-1 fusion protein, and the reporter construct has one or more Gal4 binding sites that bind the GAL4-Elk-1 fusion protein.

In these cases, as above, activation of the Elk-1 portion of the fusion protein through the MAP kinase signaling pathway leads to Gal4 controlled expression of the reporter gene. MAP kinase activation of the Elk-1 fusion protein causes the protein to bind to the Gal-4 binding sites on the reporter gene and induce reporter construct expression. Note that other Elk-1 fusion protein/reporter gene construct pairs may be used in the context of the present invention as long as mGluR mediated activation of the MAP kinase pathway induces the Elk-1 fusion protein to express the reporter construct.

Recombinant cell lines are quantitated for mGluR expression by employing assays for mGluR biological activity or by employing assays that are independent of such activity, such as Western blotting or immunoassay using antibodies that are capable of reacting with Group I mGluRs. (Sambrook et al., Molecular cloning: A laboratory manual, 1989;18.1–18.88).

Target compounds to be screened for gabapentinoid activity are synthesized as described in the NK embodiments. Compounds may be incubated with cells prior to, at the same time, or after stimulation of the mGluR receptor with mGluR agonist. In preferred embodiments, compounds are incubated with the above described cells prior to mGluR activation, suitable times are variable, but 30 to 45 minutes prior to mGluR activation is typical. Total incubation times of target compounds on the host cells is variable and set for the user's convenience as well as for the level of reporter construct expression needed for detection in the assay; however, suitable times are typically for about 3 to 6 hours and most preferably from 3.5 to 5 hours.

In general, each test compound is tested for its inhibitory activity through a range of concentrations, for example, a compound may be tested at concentrations from 25 to 1500 $\mu$M, and preferably from 50 to 1000 $\mu$M. In some embodiments of the present invention, the host cells are incubated with a single dose of target compound, for example a dose between 25 and 1500 $\mu$M, and preferably a single dose of about 450 to 550 $\mu$M.

Detection of gabapentinoid activity in a test compound is essentially as described above in the NK embodiments.

PMA Stimulation

In another aspect, the in vitro assay of the present invention is based on the discovery that gabapentinoid activity may be screened through PKC mediated Erk-2 activation. PKC competent cells are stimulated with PMA, preferably in the range of 50 nM, to activate Erk-2. Activated Erk-2, as discussed above, activates Elk-1 which induces reporter gene expression. Compounds tested for gabapentinoid activity are incubated in PMA stimulated cells and gabapentinoid activity followed through inhibition of reporter gene expression. As above, cells may be incubated with the target compound before treatment with PMA. Screening aspects are the same as discussed above. Note that this embodiment allows for the screening of gabapentinoid activity in both neuronal-like (IMR-32) cells and nonneuronal (CHO) cells, and does not require the overexpression of mGluR or NK receptors.

Erk-2 Phosphorylation

It is envisioned that other gabapentinoid detection assays be within the scope of the present invention. For example, host cells having intact MAPK signaling pathways may be used to screen compounds for gabapentinoid activity by detecting a compounds inhibitory effects on the MAP kinase signaling pathway. For example, IMR-32 cells may be treated with PMA and total Erk-2 phosphorylation determined through Western blotting. Target compounds are incubated with the PMA stimulated cells to determine the compounds inhibitory effect on Erk-2 phosphorylation and compared to a nontreated control and a gabapentin treated control. Alternatively, Erk-2 phosphorylation may be followed in cells that have intact MAPK signaling pathways where either NK or mGluR receptors are overexpressed. Erk-2 phosphorylation is achieved by treatment with substance P or quisqualate, respectively, and a target compound's inhibitory effects on Erk-2 phosphorylation correlated to gabapentinoid activity. Phosphorylation of Erk-2 may be detected using a Western blot assay, immunoprecipitation assay, etc. Note that the cell lines and methods used in this embodiment are essentially as described above.

Method of Screening a Compound for Gabapentinoid Activity

Analogs and derivatives of gabapentin are screened for gabapentinoid activity in accordance with one method of the invention. Host cells are engineered to express either NK receptor or Group I mGluR. Host cells are optionally transfected to also contain copies of an Erk-2 inducible reporter gene, for example a reporter gene responsive to the Elk-1 transcription factor. In preferred embodiments of the method, host cells having the Elk-1 inducible reporter gene are further engineered to overexpress the Elk-1 transcription factor. In other embodiments, host cells having the Elk-1 inducible reporter gene are engineered to overexpress a fusion protein having a functional Elk-1 portion and a reporter gene element DNA binding portion. Note that other Erk-2 responsive Ets family members may be substituted into the above described method.

Next, cells are separated into groups for treatment with a target analog or derivative of gabapentin (note that a negative and positive control group may be prepared in parallel with the cells used for target compound testing). Each individual group has a substantially equal number of cells for treatment with target compound. Each separate group of cells is treated with a similar concentration of target compound and allowed to incubate for 30 to 45 minutes. Optionally, a single target compound may be tested at increasing concentrations on a series of separate groups. Cells are then treated with either substance P or quisqualate, depending on whether the host cells express the NK receptor or mGluR. Cells are allowed to incubate for 3 to 6 hours. Each group of cells is harvested and reporter gene expression determined as is well-known in the art. Comparisons are made between each compound for inhibitory effects on reporter gene expression as well as against the negative and positive control.

In another embodiment of the method, NK or mGluR expressing cells and treated with compounds and agonist as above, cells are then harvested and Erk-2 phosphorylation determined (via Western blot or other well known technique). The inhibitory effects of each compound on Erk-2 phosphorylation is determined and compared to known controls.

Gabapentinoid Administration Methods

Gabapentinoids showing inhibitory activity in the in vitro assays of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

Gabapentinoids can be administered by known techniques, such as orally, parentally (including subcutaneous injection, intravenous, intramuscular, intrasternal, or infusion techniques), by inhalation spray, topically, by absorption through a mucous membrane, or rectally, in dosage unit formulations containing conventional nontoxic pharmaceutically acceptable carriers, adjuvants, or vehicles. Pharmaceutical compositions of the invention can be in the form of suspensions or tablets suitable for oral administration, nasal sprays, creams, sterile injectable preparations, such as sterile injectable aqueous or oleageneous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents, and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable nonirritating excipient, such as cocoa butter, synthetic glyceride esters, or polyethylene glycols, which are solid at ambient temperatures, but liquefy or dissolve in the rectal cavity to release the drug.

Preferred administration routes include orally, parenterally, as well as intravenous, intramuscular, or subcutaneous routes. More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin, and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions, or sterile powders comprising an active ingredient which are adapted for the extemporaneous preparation of sterile injectable or infusible solutions or dispersions. In all cases, the ultimate dosage form should be sterile, fluid, and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example: parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption, for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

The present invention may be better understood with reference to the accompanying examples that are intended for purposes of illustration only and should not be construed to limit the scope of the invention. All literature citations herein are expressly incorporated by reference.

EXAMPLE 1

Gabapentin Inhibits Rat mGluR5 Mediated ERK Phosphorylation in CHO Cells

CHO cells engineered to express mGluR5 (CHO-mGluR5 cells) were plated in 12-well tissue culture plates at a density of 20,000 cells/well and grown for 24 hours, followed by further culturing in serum free medium for 16 hours. CHO-mGluR5 cells were incubated in Krebs buffer for 30 minutes at which time 1 mM sodium pyruvate and 10 $\mu$/mL glutamic-pyruric transaminase was added. CHO-mGluR5 cells were then stimulated with quisqualic acid for 5 minutes, washed with cold PBS buffer containing 1 mM sodium orthovanadate and 1 mM phenylmethylsulfonyl fluoride, then solubilized in lysis buffer (10 mM Hepes, pH 7.4, 70 mM NaCl, 50 mM b-glycerol phosphate, 1% Triton X-100, 1 mM sodium orthovanadate, 1 mM phenylmethylsulfonyl fluoride, and 1× protease inhibitor cocktail). CHO-mGluR5 cells treated with gabapentin were pretreated with 100 $\mu$M gabapentin for 30 minutes prior to quisqualic acid stimulation. Gabapentin was prepared as outlined in Bryans et al., *Medicinal Research Reviews*, 1999;19:149–177. Proteins in cell extracts were separated by SDS-PAGE and transferred to nitrocellulose membrane. The membrane was blocked overnight at 4° C. with 4% BSA in Tris-buffered saline containing 0.2% (v/v) Tween 20 (TBST). The membrane was then incubated for 1 hour at room temperature (RT) with antiphospho MAP kinase antibody (1:1000 dilution) in 1% BSA and TBST, then washed with TBST followed by incubation with antirabbit IgG HRP antibody. After a final wash with TBST, the membrane was visualized using enhanced chemiluminescence reagents.

Results

Activation of Erk-1 and -2 by stimulating CHO-mGluR5 cells with 100 $\mu$M quisqualate was examined by using an antibody specific to phosphorylated Erk-1 and -2. As shown in FIG. 1 (Lane 1), there was little phosphorylated Erk-1 and -2 in unstimulated CHO cells. Addition of 100 μM quisqualate for 5 minutes quickly increased the level of phosphorylated Erk-2, but had little effect on changing the level of phosphorylated Erk-1 (Lane 2). Preincubation of the mGluR5/CHO cells with 100 μM gabapentin for 30 minutes reduced the quisqualate activated phosphorylated Erk-2 by 50% (Lane 4). Gabapentin treated CHO-mGluR5 cells, in the absence of quisqualate, showed little or no phosphorylated Erk-1 and -2 (Lane 3). As a positive control, PD 184352 (known MEK inhibitor) block the effect of quisquolate (data not shown).

The data from this study illustrates the utility of the present invention for screening compounds for gabapentinoid activity.

Since P38 and Jun kinases are closely related to MAP kinase, the effects of substance-P on these kinases was examined. Addition of 10 nM substance-P to cells overexpressing NK1 (CHO-NK-1 cells), significantly activated MAP kinase, but had no effect on either P38 or Jun kinase activation as determined by Western blot using activation-specific antibodies (data not shown). Also unlike CX3C receptor, NK1 has no effect on activation of AKT, indicating that AKT signaling is not involved in the gabapentin-sensitive MAP kinase pathway (data not shown). This data indicates that NK1 elicited MAP kinase signaling is a fairly specific target for screening compounds for gabapentinoid activity through the compounds ability to inhibit NK-1 elicited MAP kinase signaling.

EXAMPLE 2

Gabapentin Inhibits PMA Mediated ERK Phosphorylation in Differentiated IMR-32 Cells IMR-32 cells were grown in MEM media (Gibco BRL, 11095-080), supplemented with 10% fetal bovine serum (Gibco BRL, 26140-087), 1% antibiotic-antimycotic (Gibco BRL, 15240-096), and 1% L-glutamine (Gibco BRL, 25030-032). Cells, grown to confluency, were differentiated for a period of 7 to 10 days, or longer, by adding 1 mM dibutyryl cAMP (Sigma D-0627) and 2.5 μM 5-bromo-2-deoxyuridine (Sigma B-9285) to the media. The differentiation media was fed continuously to cells until the cells were used in an experiment. Cells were divided into groups and preincubated for 30 minutes either in the presence or absence of indicated concentration of gabapentin then subsequently challenged with 50 nM PMA for 5 minutes. Cells were washed with cold PBS buffer containing 1 mM sodium orthovanadate and 1 mM phenylmethylsulfonyl fluoride, then solubilized in lysis buffer (10 mM Hepes, pH 7.4, 70 mM NaCl, 50 mM b-glycerol phosphate, 1% Triton X-100, 1 mM sodium orthovanadate, 1 mM phenylmethylsulfonyl fluoride, and 1× protease inhibitor cocktail). Proteins in cell extracts were separated by SDS-PAGE and transferred to nitrocellulose membrane. The nitrocellulose membrane was blocked overnight at 4° C. with 4% BSA in Tris-buffered saline containing 0.2% (v/v) Tween 20 (TBST). The membrane was then incubated for 1 hour at RT with antiphospho MAP kinase antibody (1:1000 dilution) in 1% BSA and TBST, then washed with TBST followed by incubation with antirabbit IgG HRP antibody. After a final wash with TBST, the membrane was visualized using enhanced chemiluminescence reagents.

Results

Figure 2:
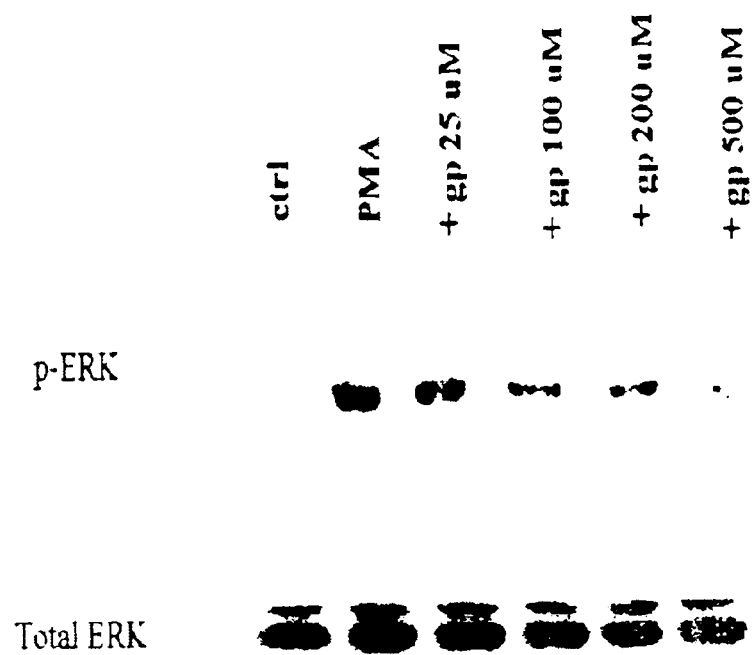
FIG. 2 shows the dose-dependent effects of gabapentin on PMA mediated Erk-2 phosphorylation in differentiated IMR-32 human neuroblastoma cells. Differentiated IMR-32 cells were pretreated with indicated concentrations of gabapentin for 30 minutes and then stimulated with PMA for 10 minutes. Products from treated cells were analyzed by Western blotting with anti-pErk antibody.

To determine the biological relevance of gabapentin effects on the MAP kinase pathway, differentiated IMR-32 cells treated with PMA were examined. As shown in FIG. 2, treatment with PMA (50 μM) increased Erk-2 phosphorylation (upper panel) in differentiated IMR-32 cells, and the effects were dose-dependently blocked by gabapentin. As controls, the lower panel showed that the total amount of Erk-1 and -2 in all samples are the same. Since differentiated IMR-32 cells have many characteristics of a neuronal cell type, these data indicate that gabapentin effects on the MAP kinase pathway are a biologically relevant phenomena. These data also indicate that mGluR5 is not the direct target of gabapentin, since gabapentin showed similar inhibitory effects when MAP kinase was activated by PKC instead of through mGluR5 (not shown).

The data from this Example illustrates the utility of the present invention in that inhibitory gabapentinoid activity on MAP kinase is dose dependent and can be tested on multiple cell types that have MAP kinase activity.

EXAMPLE 3

In Vitro Screen for Gabapentinoid Activity

CHO-NK-1 cells were seeded to plates and grown to confluency overnight. Lipofectamine transfection was performed on the confluent cells to insert Elk-1 and luciferase vectors necessary for a MAP kinase dependent reporter system. Prior to transfection, the cells were washed in OPTI media (Gibco). To each confluent well in a 24-well plate, 20 ng of Elk-1 and 200 ng of luciferase DNA vectors were added. In addition to the vectors, 1.5 μL of Lipofectamine Reagent (Gibco) and OPTI media (Gibco) were also added for a total transfection volume of 200 μL (a master mix was made prior to use). After a 3-hour incubation, the media was changed to F-12 growing media (500 μL/well) for an additional 3-hour incubation. After the second incubation, the media was changed again to DMEM (500 μL/well) for serum starvation and incubated overnight (all incubations at 37° C.).

In addition, lipofectamine transfection was performed on CHO-NK-1 confluent cells to insert a GAL4-Elk-1 fusion protein and luciferase vector using the methods described above.

Luciferase Assay

The DMEM media was decanted off the plate, and the cells were washed with 500 μL of Kreb buffer. After the wash, 460 μL of Kreb buffer containing 2 mM sodium pyruvate was added to each well and incubated for 30 minutes at 37° C. Next, 20 μL of compound was added to each well at the desired concentration and incubated for another 30 minutes. Note that gabapentin was prepared as discussed in Bryans et al., Medicinal Research Reviews, 1999; 19:149–177, pregabalin was prepared as outlined in Hoekstra et al., Org. Process Res. Dev., 1997;1(1):26–38 and PD 201698 and PD 200390 were prepared as outlined in International Patent Application WO 9921828. Finally, the cells were stimulated with Substance-P (final concentration= 20 nM), and the cells were incubated for 4 hours at 37° C. After the 4-hour incubation, the buffer was decanted off the plate, and the plate was washed twice with Dulbecco's-PBS. Cells were lysed with 100 μL per well of cell Lysis Buffer (Promega), and the plate was vortexed for 10 minutes. Finally, 10 μL of the cell lysate was transferred to a 96-well reader plate, and each well's luminescence was measured using a luminometer (the Promega Luciferase Reporter system was used).

Note that the 24-well assay format may be modified into a 96-well assay format for higher throughput capabilities. In the 96-well format the assay is modified by scaling down the 24-well format 4-fold. Therefore, each well in the 96-well format has one fourth the amount of reagents as the 24-well assay format. A permanent CHO cell line has also been created by electroporation of the NK-1, Elk-1, and luciferase vectors, thus circumventing the need for lipofectamine transfection.

Results

A major downstream target for MAP kinase is the activation of the Elk-1 transcription factor. Therefore, the effects of gabapentin and pregabalin were examined on Elk-1 mediated reporter gene activation.

Figure 3:
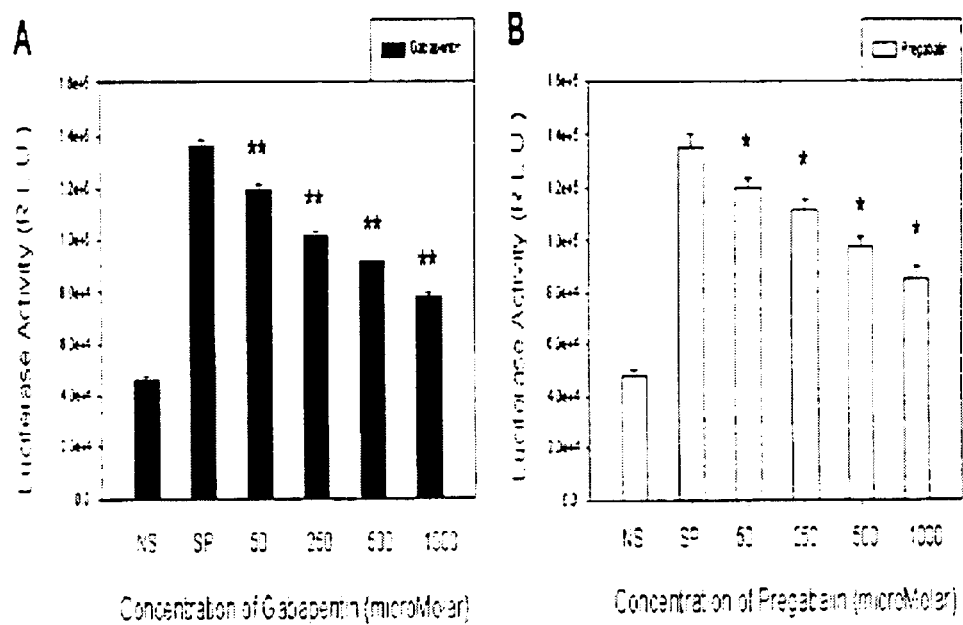
FIGS. 3A and 3B are graphs showing the dose-dependent inhibitory effects of gabapentin (A) and pregabalin (B) on NK1 mediated Elk-1 transcription. Relative light units (Y axis) indicate luciferase activity in the presence of increasing concentrations of gabapentin or pregabalin (X axis).
Figure 3A:
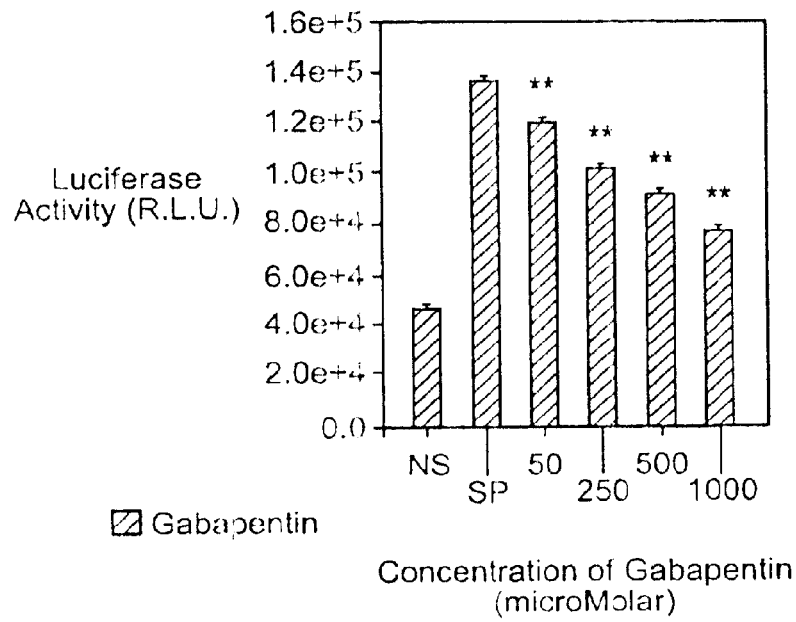
Figure 3B:
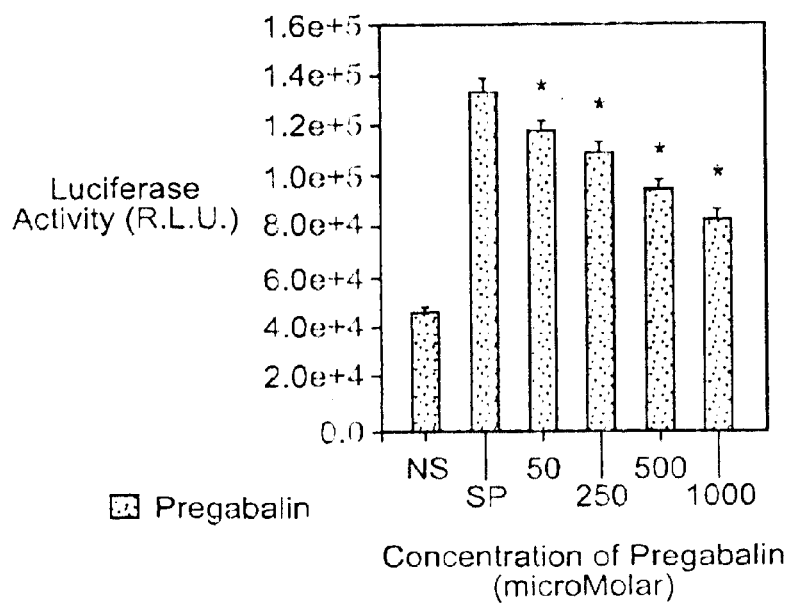

Using the luciferase assay system discussed above, both gabapentin and pregabalin showed dose dependent inhibition of the Elk-1 mediated reporter gene (elicited by substance P) (FIG. 3). In particular, substance P treated CHO/NK-1 cells showed significant Elk-1 mediated luciferase activity. However, treatment of the CHO/NK-1 cells with both substance P and gabapentin (FIG. 3A) or pregabalin (FIG. 3B) showed dose dependent inhibition of the Elk-1 mediated luciferase activity.

Although the Elk-1 mediated luciferase assay is not a direct measure of gabapentin activity, as was measuring for phosphorylated Erk-1 and -2 (Examples 1 and 2), the Elk-1 reporter gene assay is highly quantitative and provides a high-throughput assay for screening numerous compounds for gabapentinoid acitivy.

To determine whether there is a correlation between the inhibitory effects of gabapentinoids on Elk-1 mediated reporter gene activation and the gabapentinoids biological efficacy in vivo, two pharmacologically well-characterized gabapentinoids were tested for inhibitory effects on Elk-1 mediated luciferase activity. As shown in FIG. 4 (left panel), PD 200390, a potent gabapentinoid in in vivo animal pain models, showed dose-dependent inhibition on Elk-1 mediated luciferase activity. In contrast, PD 201698, a biologically inactive enantimer of PD 200390, displayed little inhibition of luciferase expression (right panel). As a positive control, the potent MEK inhibitor PD 148352 was included in the assay, and it completely inhibited the Elk-1 mediated activity (last column in both panels).

The stereo-specificity illustrated by this Example illustrates that the Elk-1 inducible reporter system is not only useful for evaluating the effects of gabapentin analogues and derivatives on MAP kinase activation, but is useful in the prediction of biological in vivo effects of target gabapentinoids.

Figure 5:
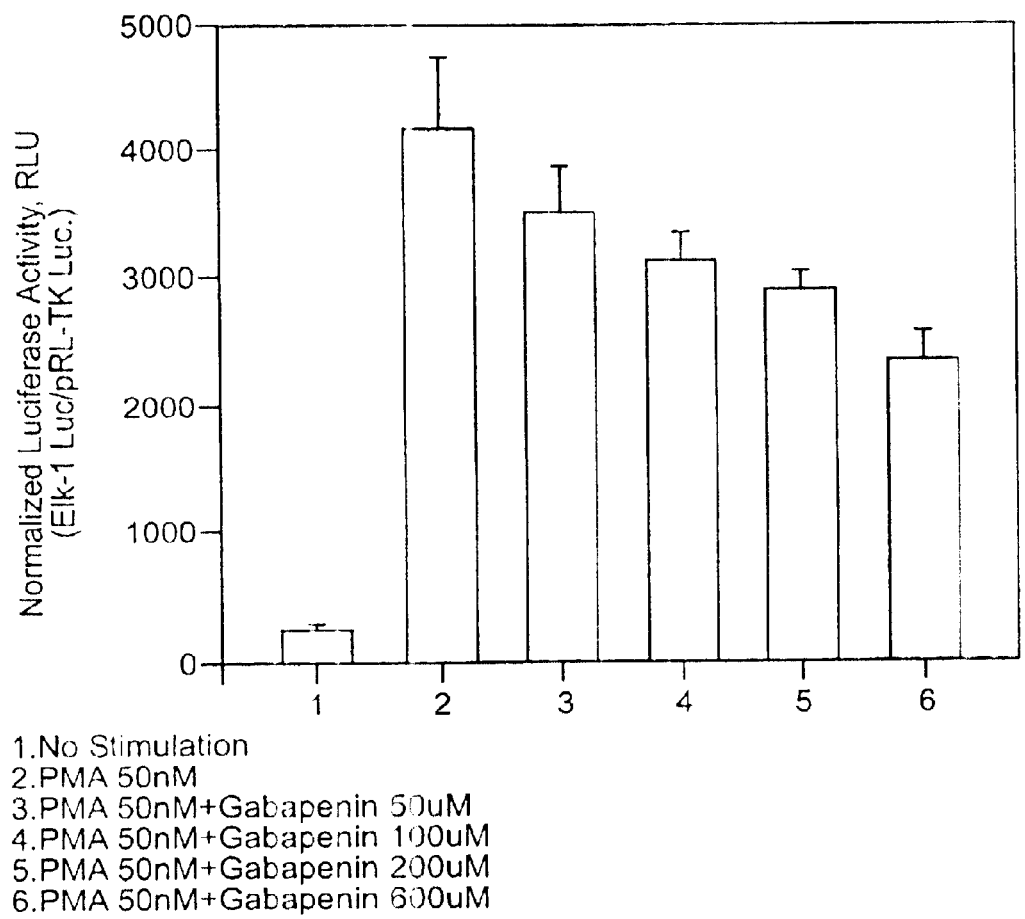
FIG. 5 is a graph showing the dose-dependent inhibitory effects of gabapentin on PMA mediated Elk-1 transcription in IMR-32 cells. Relative light units (Y axis) indicate luciferase activity in the presence of increasing concentrations of gabapentin or pregabalin (X axis).
Figure 6:
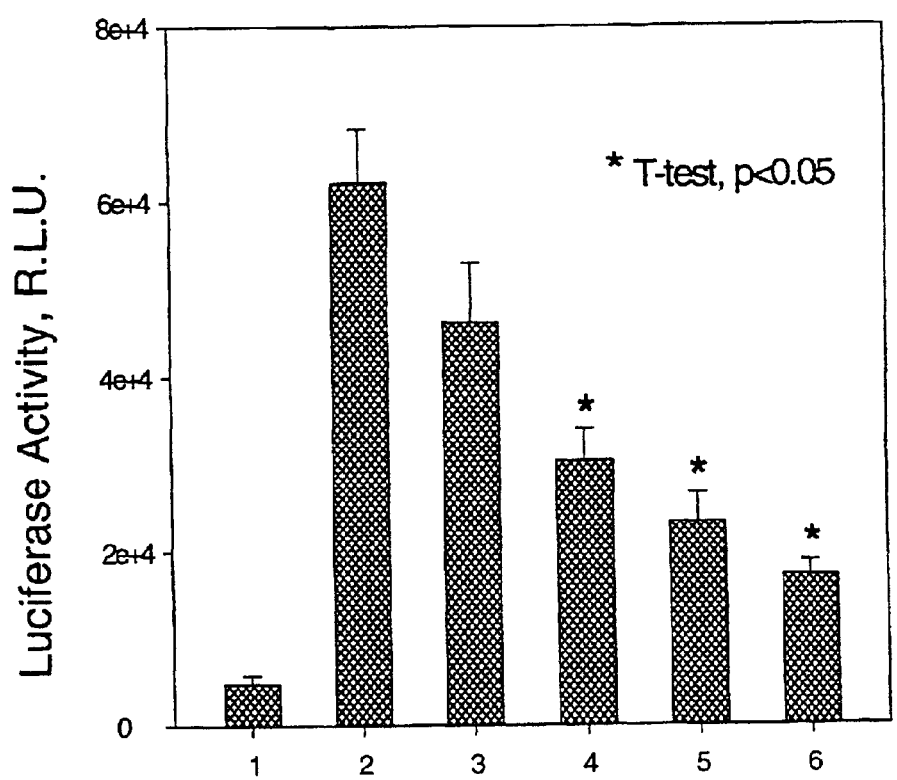
FIG. 6 is a graph showing the dose-dependent inhibitory effects of gabapentin on PMA mediated Elk-1 transcription in CHO cells. Relative light units (Y axis) indicate luciferase activity in the presence of increasing concentrations of gabapentin or pregabalin (X axis).

To further substantiate the general applicability of these in vitro assay systems, the effects of gabapentin on PMA stimulated Elk-1 activation in IMR-32 cells was studied. As shown in FIG. 5., 50 nM PMA significantly increased Elk-1 mediated activity in IMR-32 cells. Addition of gabapentin dose-dependently decreased the effects of PMA-induced reporter gene expression. This data is consistent with the previously observed inhibitory effects of gabapentin on Erk-2 phosphorylation in differentiated IMR-32 cell (FIG. 2). Similarly, PMA activated reporter gene activity in CHO cells, and gabapentin, in a dose-dependent manner, reduced the PMA mediated effects (FIG. 6).

These data show that numerous cell lines, including neuronal-like (IMR-32) and nonneuronal (CHO), may be used as host cells for screening compounds for gabapentinoid activity. The fact that gabapentinoid activity can be observed in cells stimulated with either receptor agonist (substance P) or PKC activator (PMA) strongly suggested that the target for gabapentin is a signaling molecule downstream from receptors and PKC.

Figure 7:
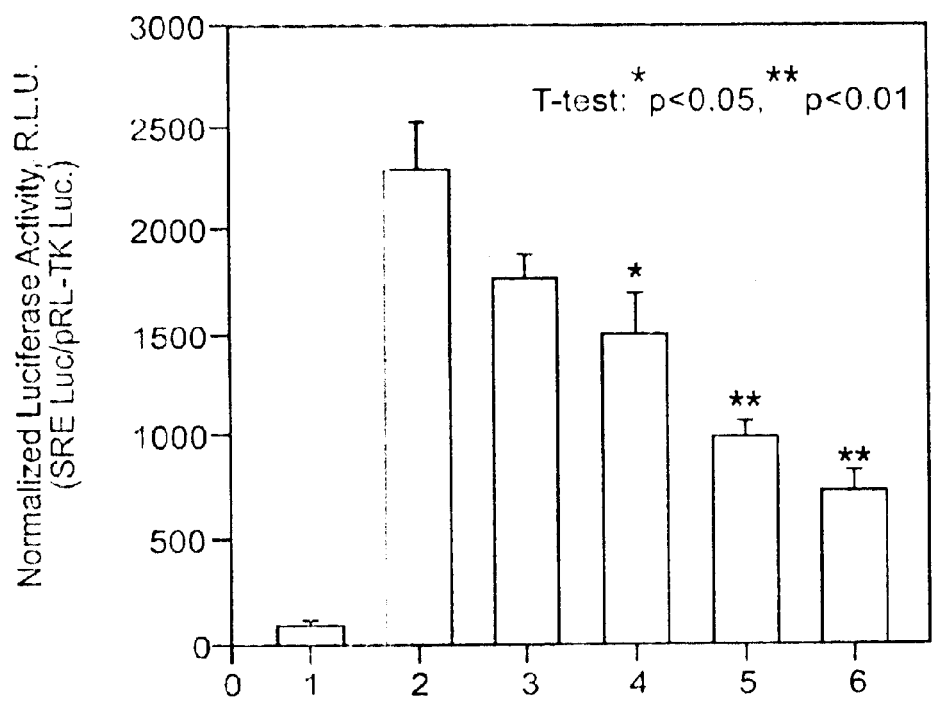
FIG. 7 is a graph showing the dose-dependent inhibitory effects of gabapentin on NK1 mediated SRE activation. Relative light units (Y axis) indicate luciferase activity in the presence of increasing concentrations of gabapentin or pregabalin (X axis).

Note that due to the necessity of transfecting two plasmids in the Elk-1 reporter gene assay (Elk-1 or a Elk-1 fusion protein overexpressed) and the variability associated with the a 2-plasmid co-transfection method, an alternative reporter system requiring transfection of only one plasmid has been developed. NK-1 expressing cell line were transfected with a reporter construct having a series of SRE binding elements. NK-1 expressing cells had endogenous levels of the Elk-1 transcription factor. As shown in FIG. 7, gabapentin showed similar potency in this "SRE-based reporter system," where results were similar to data seen in the other "two plasmid" co-transfection assays. These data indicates that the SRE assay is another useful assay system for evaluating the biological activities of gabapentinoids.

Finally, to improve the Elk-1 mediated luciferase assay, three permanent cell lines have been developed, each one expressing a different level of a Gal4/Elk-1 fusion transcription factor and each one containing different copy numbers of the Gal4-controlled luciferase genes. Using these permanent cell lines, the inducible reporter gene assay can be performed without prior transfection and effectively eliminates the variations associated with the transient tranfection method.

It will be clear that the present invention is well-adapted to attain the ends and advantages mentioned as well as those inherent therein. While a presently preferred embodiment has been described for purposes of this disclosure, numerous changes may be made which will readily suggest themselves to those skilled in the art. Accordingly, all such modifications, changes and alternatives are encompassed in the spirit of the invention disclosed and as defined in the appended claims.

What is claimed is:

1. A method for detecting gabapentinoid activity in a test compound comprising the steps of:
 (a) introducing into host cells that express an NK receptor a heterologous DNA sequence that encodes a reporter polypeptide which responds to Erk-2 activation;
 (b) separating the host cells into at least two groups, a first group and a second group;
 (c) treating the first group of host cells with a test compound that binds to the $\alpha_2\delta$ subunit of a calcium channel;
 (d) treating the first group and second group of host cells with an NK receptor agonist;
 (e) determining reporter polypeptide activity in the first group and in the second group; and
 (f) comparing reporter polypeptide activity from the first group to the second group; and
 (g) identifying as a gabapentinoid, a test compound that shows greater inhibition of said reporter polypeptide activity in said first group of step f) than said reporter polypeptide activity of said second group in step f).

2. The method of claim 1, wherein the host cells are Chinese hamster ovary (CHO) cells.

3. The method of claim 1, wherein the heterologous DNA sequence encodes luciferase.

4. The method of claim 1, wherein in the NK receptor agonist is substance P.

5. The method of claim 1, wherein step (b) comprises the step of separating the host cells into a plurality of groups, and step (c) comprises treating each separate group with a compound having a final concentration of between 1 $\mu$M and 1 mM.

6. The method of claim 1, wherein step (d) occurs prior to step (c).

7. A method for detecting gabapentinoid activity in a test compound comprising the steps of:
   (a) introducing into host cells that express the an NK1 receptor a heterologous DNA sequence that encodes a reporter polypeptide which responds to Erk-2 activation;
   (b) separating the host cells into at least two groups, a first group and a second group;
   (c) treating the first group of host cells with a test compound that binds to the $\alpha^2\delta$ subunit of a calcium channel;
   (d) treating the first group and second group of host cells with an NK receptor agonist;
   (e) determining reporter polypeptide activity in the first group and in the second group;
   (f) comparing reporter polypeptide activity from the first group to the second group; and
   (g) identifying as a gabapentinoid, a test compound that greater inhibition of said reporter polypeptide activity in said first group of step f) than said reporter polypeptide activity of said second group in step f).

8. A method for detecting gabapentinoid activity in a target compound comprising the step of:
   (a) introducing into host cells that express an NK receptor a heterologous DNA sequence chat encodes a reporter polypeptide which responds to Erk-2 activation;
   (b) separating the host cells into at least two groups, a first group and a second group;
   (c) treating the first group of host cells with a target compound;
   (d) treating the first group and second group of host cells with an NK receptor agonist;
   (e) determining reporter polypeptide activity in the first group and in the second group;
   (f) comparing reporter polypeptide activity from the first group to the second group; and
   (g) identifying as a gabapentinoid, a target compound that shows greater inhibition of said reporter polypeptide activity in said first group of step f) than said reporter polypeptide activity of said second group in step f); wherein said target compound is a compound of formula

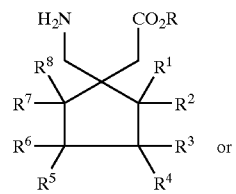

1

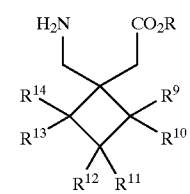

1A or R5 a2 1 1A or a pharmaceutically acceptable salt thereof wherein:
R is hydrogen or a lower alkyl;
(h) R1 to R14 are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, —CO2H, —CO2R15, —CH2CO2H, —CH2CO2R15, —OR15 wherein R15 is a straight or branched alkyl of from 1 to 6 carbons, phenyl, or benzyl, and R1 to R8 are simultaneously hydrogen.

9. The method of claim 1 wherein said test compound of step g) shows, at 500 $\mu$M, at least 20% greater inhibition of said reporter polypeptide activity in said first group of step f) than said reporter polypeptide activity of said second group in step f).

10. The method of claim 1 wherein said test compound of step g) show, at 500 $\mu$M, at least 25% greater inhibition of said reporter polypeptide activity in said first group of step f) than said reporter polypeptide activity of said second group in step f).

11. The method of claim 1 wherein said test compound of step g) shows, at 500 $\mu$M, at least 30% greater inhibition of said reporter polypeptide activity in said first group of step f) than said reporter polypeptide activity of said second group in step f).

* * * * *